(12) United States Patent
Pooley et al.

(10) Patent No.: US 12,186,069 B2
(45) Date of Patent: Jan. 7, 2025

(54) SENSING SYSTEM AND METHOD

(71) Applicant: TTP Plc, Royston (GB)

(72) Inventors: David Pooley, Royston (GB); Mikhail Bashtanov, Royston (GB)

(73) Assignee: TTP PLC, Royston (GB)

( * ) Notice: Subject to any disclaimer, the term of this patent is extended or adjusted under 35 U.S.C. 154(b) by 1082 days.

(21) Appl. No.: 16/332,399

(22) PCT Filed: Sep. 18, 2017

(86) PCT No.: PCT/GB2017/052760
§ 371 (c)(1),
(2) Date: Mar. 12, 2019

(87) PCT Pub. No.: WO2018/051129
PCT Pub. Date: Mar. 22, 2018

(65) Prior Publication Data
US 2020/0060578 A1    Feb. 27, 2020

(30) Foreign Application Priority Data
Sep. 16, 2016 (GB) ...................................... 1615847

(51) Int. Cl.
*A61B 5/00* (2006.01)
*A61B 5/06* (2006.01)
(Continued)

(52) U.S. Cl.
CPC ................ *A61B 5/062* (2013.01); *G01V 3/10* (2013.01); *G01V 15/00* (2013.01)

(58) Field of Classification Search
CPC ...................... G01V 15/00; A61B 2034/2051; A61B 5/061; A61B 5/062; A61B 5/063
See application file for complete search history.

(56) References Cited

U.S. PATENT DOCUMENTS

| 4,704,602 A | 11/1987 | Asbrink | |
|---|---|---|---|
| 2001/0045826 A1* | 11/2001 | Schneider | ............ G01D 5/2073 324/207.17 |

(Continued)

FOREIGN PATENT DOCUMENTS

| GB | 2104099 A | 3/1983 |
|---|---|---|
| WO | 2011095916 A1 | 8/2011 |
| WO | 2014072854 A1 | 5/2014 |

OTHER PUBLICATIONS

PCT Patent Application PCT/GB2017/052760 International Search Report dated Nov. 16, 2017.
(Continued)

*Primary Examiner* — Rajeev P Siripurapu
(74) *Attorney, Agent, or Firm* — Erise IP, P.A.

(57) ABSTRACT

A sensing system for determining the location and orientation of an object which comprises a magnetic tag. The sensing system comprises selection coils and interrogation coils. The selection coils are arranged to generate a spatially-varying DC magnetic field from which the location of the tag can be determined in use. At least some of the interrogation coils are arranged to generate one or more AC magnetic fields and at least some of the interrogation coils are arranged to receive harmonics, intermodulation products or time dependent variations of the AC magnetic fields, from which the orientation of the tag is determined in use.

17 Claims, 17 Drawing Sheets

(51) Int. Cl.
 *G01V 3/10* (2006.01)
 *G01V 15/00* (2006.01)

(56) References Cited

U.S. PATENT DOCUMENTS

| | | | | |
|---|---|---|---|---|
| 2006/0122497 | A1* | 6/2006 | Glossop | A61B 34/20 |
| | | | | 600/424 |
| 2006/0247511 | A1* | 11/2006 | Anderson | A61B 5/062 |
| | | | | 600/407 |
| 2008/0218162 | A1* | 9/2008 | Ruhrig | A61B 5/05 |
| | | | | 324/228 |
| 2010/0033173 | A1* | 2/2010 | Gleich | A61B 5/05 |
| | | | | 324/228 |
| 2015/0115944 | A1* | 4/2015 | Ashe | G01D 5/2073 |
| | | | | 324/232 |
| 2016/0246369 | A1* | 8/2016 | Osman | A63F 13/212 |
| 2017/0067972 | A1* | 3/2017 | Diamond | G01R 33/1276 |

OTHER PUBLICATIONS

PCT Patent Application PCT/GB2017/052760 Written Opinion of the International Search Authority dated Nov. 16, 2017.
S. Tumanski, "Handbook of Magnetic Measurements," pp. 1-68; Routledge Handbooks Online, Jun. 2011.

\* cited by examiner

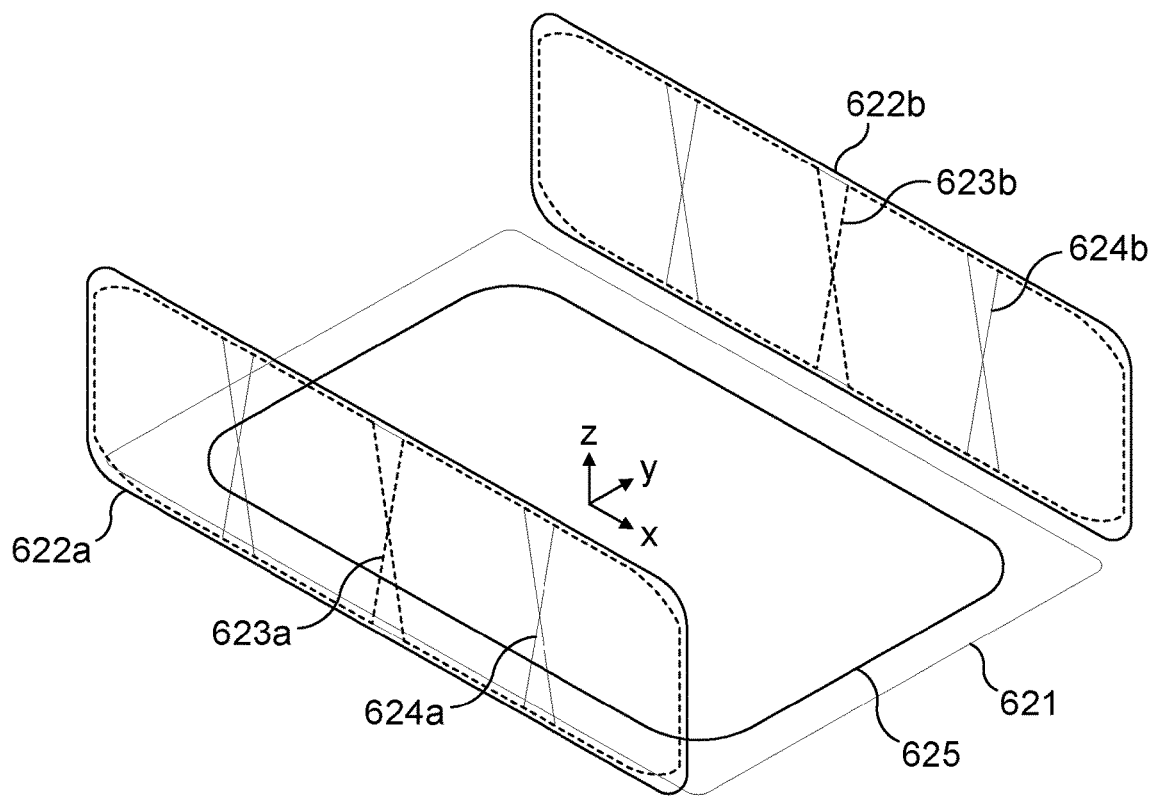
Figure 6c
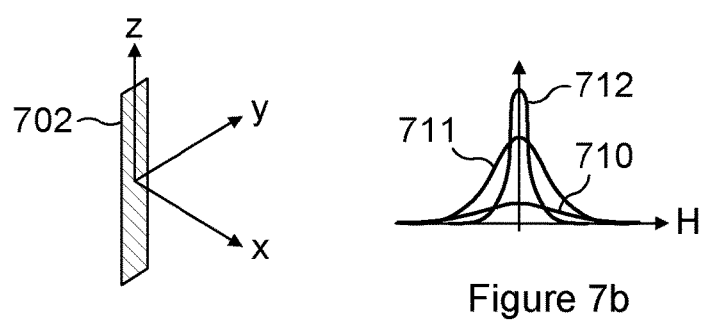
Figure 7a
Figure 7b
Figure 7c

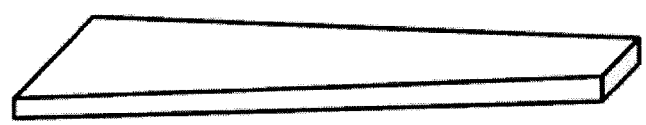
Figure 8a
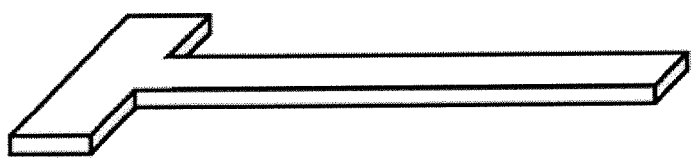
Figure 8b
Figure 8c
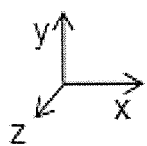

SENSING SYSTEM AND METHOD

RELATED APPLICATIONS

The present application is a national stage application under 35 U.S.C. § 371 of International Application No. PCT/GB2017/052760, filed 18 Sep. 2017, which claims priority to Great Britain Patent Application No. 1615847.9, filed 16 Sep. 2016. The above referenced applications are hereby incorporated by reference into the present application in their entirety.

FIELD OF THE INVENTION

This invention relates to a sensing system and method for determining the location and orientation of an object which comprises a magnetic tag, for example within a body during medical and surgical procedures. Examples of objects which may be located or tracked include catheters, endoscopes and endoscopic capsules.

BACKGROUND

It is often required to track the location of catheters, endoscopic capsules and the like during medical procedures, in order to ascertain their location and orientation. Real-time location relative to other structures, for example by overlaying location data on x-ray CT or MRI scan data is often beneficial to help guide procedures.

Commercial electromagnetic tracking methods typically either use a permanent magnet or a search coil within the patient. In the first case, the permanent magnet is located by an array of magnetic field sensors, external to the patient. The magnitude and angle of the magnetic field is used to infer the position of the permanent magnet. Such systems are limited by a requirement for a permanent magnet of several cubic millimetres in volume in order to produce a measurable signal, susceptibility to external magnetic fields (such as the earth's field), and inability to track multiple targets.

In the second case, external transmitter coils produce time-varying (AC) magnetic fields and an inductive pick-up coil (search coil) is located within the patient, in which a voltage is induced. Location is inferred by the (known) properties of the transmitted fields. Such systems also require an internal coil several cubic millimetres in volume, as well as requiring voltages (or data) to be retrieved from the search coil in order for real-time location to be possible. Operation frequency (and hence, signal strength) is limited by the need to avoid distortion in the transmitted fields, for example due to induced eddy current in tissue and other nearby conductive materials.

As an alternative, the non-linear magnetic response of spherical magnetic particles has been used to produce odd harmonics of an AC field. This specifically deals with bio-absorbable superparamagnetic iron oxide nanoparticles in the size range of some tens of nanometres. Spatial selection is accomplished by adding a DC gradient field, so that particles are detected when in the zero field region. Particles have a low aspect ratio (i.e. are substantially spherical) and particle orientation is not detected. However this technique requires very large heavy interrogation coils and has a small sample volume, unsuitable for surgical applications. This may be why this technique seems never to have been proposed for the tracking of catheters and the like.

As a separate technology high aspect ratio ferromagnetic tags with non-linear magnetisation properties have been applied as retail security tags, detecting either harmonics (GB 2,104,099) or intermodulation products (U.S. Pat. No. 4,704,602). Given the nature of the application of this only the presence of a tag is detected in this application, not its location and orientation.

SUMMARY OF THE INVENTION

According to an aspect of the invention, there is provided a sensing system for determining the location and orientation of an object which comprises a magnetic tag, the sensing system comprising selection coils and interrogation coils, wherein:
the selection coils are arranged to generate a spatially-varying DC magnetic field from which the location of the tag can be determined in use;
at least some of the interrogation coils are arranged to generate one or more AC magnetic fields; and
at least some of the interrogation coils are arranged to receive harmonics, intermodulation products or time dependent variations of the AC magnetic fields, from which the orientation of the tag is determined in use.

According to another aspect of the invention, there is provided a method of locating an object within a human or animal body, comprising the steps of:
attaching a high aspect ratio ferromagnetic tag to the object to be located;
determining the position of the ferromagnetic tag by locating the tag at a location in a spatially-varying DC magnetic field; and
determining the orientation of the tag by sensing an AC response using coils which are sensitive to different vector directions for AC magnetic field.

The invention therefore provides a system with accurate location and orientation yet which can employ a tag which is easily integrated into a medical component. For example a ferromagnetic ribbon or wire of material may be used having high magnetic permeability and preferably low coercivity, such as an amorphous or nanocrystalline alloy (e.g. Metglas 2826 MB or the Vacuumschmeltze VITROVAC or VITROPERM materials) as the moveable item with the body (hereafter, the tag or label). This can be significantly smaller than the Ø1 mm×10 mm size typical of current systems. A highly extended aspect ratio is preferred to improve signal and orientation sensing performance, e.g. a 0.005 mm×0.1 mm×5 mm ribbon, having an aspect ratio of 1000:1 between short and long edges is suggested as a possible size for this application. The high aspect ratio reduces the self-demagnetisation effect and so increases the effective magnetic permeability of the tag. This is in contrast to the low aspect ratio, nanometre-scale superparamagnetic particles used in MPI. A static or slowly varying "selection field" (also called DC gradient field or bias field) can be used to locate the tag. The tag becomes magnetically saturated quite easily and so has a non-linear response close to the zero of the selection field which is beneficial.

Typically the DC bias field is swept in order to locate the tag while the response to an AC "interrogation field" is monitored. The selection field typically takes the form of a "swept-DC" or "slowly varying" gradient field, with the variation being slow relative to the AC measurement frequency. A field-free point (FFP) or field-free line (FFL) can be generated and moved to search for the location of the tag. A simple coil configuration to achieve this is coil pairs in the x, y, and z axes, which are operated as Maxwell coils (currents in opposition) with varying current magnitudes between the coils to move the field-free point. Three or four Maxwell coil pairs are typically used to generate and rotate a field-free line within a plane.

Once located, the tag orientation (or orientations) can be determined and tracked by iteratively adjusting the selection field to the track the peak of the AC response. This iterative approach has the advantage of being able to achieve a higher frame rate than performing a full scan for every frame.

Many prior art AC location systems are restricted to operation in the frequency ranges around tens of kilohertz in order to minimise distortion of the AC field by induced eddy currents and resulting loss of positional accuracy. As the system of the invention uses the slowly varying selection field to locate the tag, a higher frequency AC interrogation field can be used without loss of positional accuracy. The use of a higher AC frequency is advantageous, as it provides a larger received voltage, a higher signal to noise ratio, and enables the use of lightweight, open sensing coils. The AC frequency is typically limited by the tag material and shape—typically somewhere in the range $10^4$ to $10^6$ Hz for amorphous or nanocrystalline tags.

When near the zero of the bias field, odd harmonics (H3=3*$f_0$, H5=5*$f_0$, etc.) of the AC frequency $f_0$ are produced, due to the non-linear magnetisation curve of the tag. When the bias field is close to the corner of the B-H curve, even harmonics (H2=2*$f_0$, H4=4*$f_0$, etc.) are generated. These harmonics may be detected to find the location of the tag. Use of the even harmonics has the benefit that the magnitude of the AC field can be smaller, as the corner of the B-H curve is quite pronounced and the AC field only needs to push the magnetisation just into and out of saturation. Use of the even harmonics has the additional benefit that a zero of field is not required, which makes location with single-sided coils more straightforward.

Alternatively two or more AC interrogation frequencies ($f_1$, $f_2$, ...) are used. The non-linear magnetisation of the tag then produces intermodulation products of the AC interrogation frequencies at frequencies n*$f_1$+m*$f_2$, where n and m are positive or negative integers (e.g. 2*$f_1$+$f_2$, 2*$f_2$+$f_1$, 3*$f_2$+2*$f_2$, 3*$f_2$+2*$f_1$, etc.). This approach has the benefit that these frequencies can be measured with a very low noise floor, as they tend not to be produced accidentally by the AC sources. Advantageously, detection frequencies well-separated from the interrogation frequencies are used (i.e. 2*$f_1$+$f_2$ rather than 2*$f_1$−$f_2$) in order to allow sufficient bandwidth for interrogation frequencies to be filtered out by the detector circuit.

A wide range of characteristic B-H curves and frequency responses may be designed by altering the chemical composition and post-processing of amorphous strips that would allow the system to distinguish between different strips and other ferromagnetic objects by measuring the characteristic spectra and their dependence on the field strength. The low coercivity and high permeability of the strips used as tags allows detection at moderately low field strengths and clear differentiation from magnetic steels which might be present in the region of the fields.

AC fields are generated and detected by a plurality of AC coils. Some of these coils are preferably mutually orthogonal coils (i.e. their mutual inductance $M_{12}$ is small, or the coupling factor k=$M_{12}/\sqrt{L_1 L_2}$ is close to zero |k|<<1). Other AC coils may be arranged specifically to produce orthogonal fields (i.e. field vectors which are at right angles to one another) within part of the sensed region. These two arrangements are referred to more generally as orthogonal coils, since many mutually orthogonal coil arrangements also produce approximately orthogonal fields throughout a reasonable volume. Transmit fields and receive angle sensitivities may be rotated by vector addition of signals on orthogonal coils.

Orientation of the tags may be detected by:
Cross-coupling of orthogonal transmit and receive coils. The cross-coupling is maximised when the easy magnetisation axis of the tag is mid-way between the two field angles.
Cross-coupling of orthogonal pairs of transmit coils, transmitting at different frequencies, such that intermodulation products are produced by the non-linear properties of the tag. Similarly, the cross-coupling is maximised when the easy magnetisation axis of the tag is mid-way between the two field angles.
Measuring the line-widths of the AC response to selection field sweeps in different axes (x,y,z), which indicates the degree of shape anisotropy of the tag in each axis, which in turn indicates the alignment of tag;
Orienting the DC bias field along a vector aligned with tag, as determined by the maximum tag response or minimum line-width as the bias field is swept;
Using a pair of tags to define an orientation vector (or three tags to define all three rotation axes).
Measuring the size of the tag by producing a small FFP and moving it along the long axis of the tag.

The line-width is defined here as the way the AC response changes in response to changing bias field—a smaller line-width is characteristic of a lower saturation field. Combinations of the techniques can be beneficial, for example to make it easier to measure all three rotation axes of an object.

Preferably, the gradient field is pulsed for lower average power input. This has the advantage of requiring less weight of copper for the coils, allowing a lower cost and more open coil arrangement.

Advantageously, some or all of the coils are single-sided, to allow greater access to the patient.

Advantageously, additional reference tags can be attached to the patient to allow imaging systems to compensate for patient movement when overlaying real-time tag positions on previously acquired x-ray CT or MRI data.

BRIEF DESCRIPTION OF THE DRAWINGS

The invention will now be described, by way of example, with reference to the accompanying figures in which:

FIGS. 6a-c relate to detection of the orientation of a tag;

FIGS. 7a-c relate to detection of the orientation of a tag;

FIGS. 8a-c show tag arrangements;

DETAILED DESCRIPTION

Figure 1:
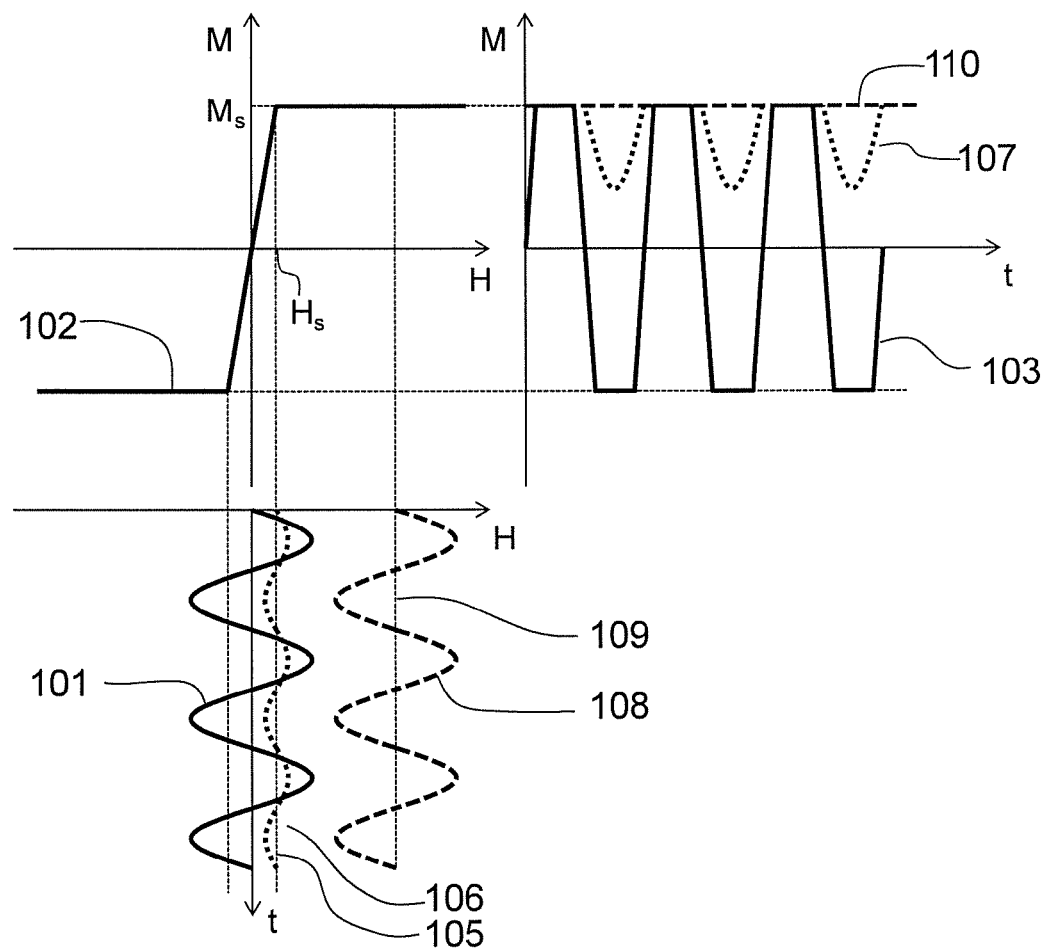
FIG. 1 illustrates the non-linear magnetisation process employed by the invention.

FIG. 1 illustrates the non-linear magnetisation process and associated generation of harmonics employed in the invention. Three cases are illustrated on this plot. The lower plot shows the time-varying application of an excitation field 101 of frequency $f_1$ (heavy solid trace). This field is applied to a tag with a non-linear magnetisation curve 102, M vs. H in the upper left plot. When the field exceeds $H_s$, the magnetisation of the tag material is saturated. The resulting tag magnetisation 103 is shown as a solid line in the upper right plot. This contains odd harmonics (H3=3*$f_1$, H5=5*$f_1$, etc.) of the fundamental excitation signal 101. In the second case, a small (effectively static) selection field 105, approximately equal to $H_s$, is present in combination with the excitation field 106 (heavy dotted line). Here, the magnetisation 107 also contains even harmonics (H2, H4 etc.). In the third case, the quasi-static selection field 109 is significantly larger than $H_s$ and the excitation field superimposed upon it 108 does not take the tag out of the saturation regime. In this case, the tag magnetisation 110 remains constant and no signal is received from the tag. As a variation on the first case, if multiple frequencies are present in the excitation signal (e.g. $f_1$ and $f_2$), non-linear mixing products (e.g. $2*f_1-f_2$, $2*f_2-f_1$) will also be present in the magnetisation. Hence, the use of a spatially varying the selection field can be used to locate a tag from its generation of non-linear mixing products.

Figure 2A:
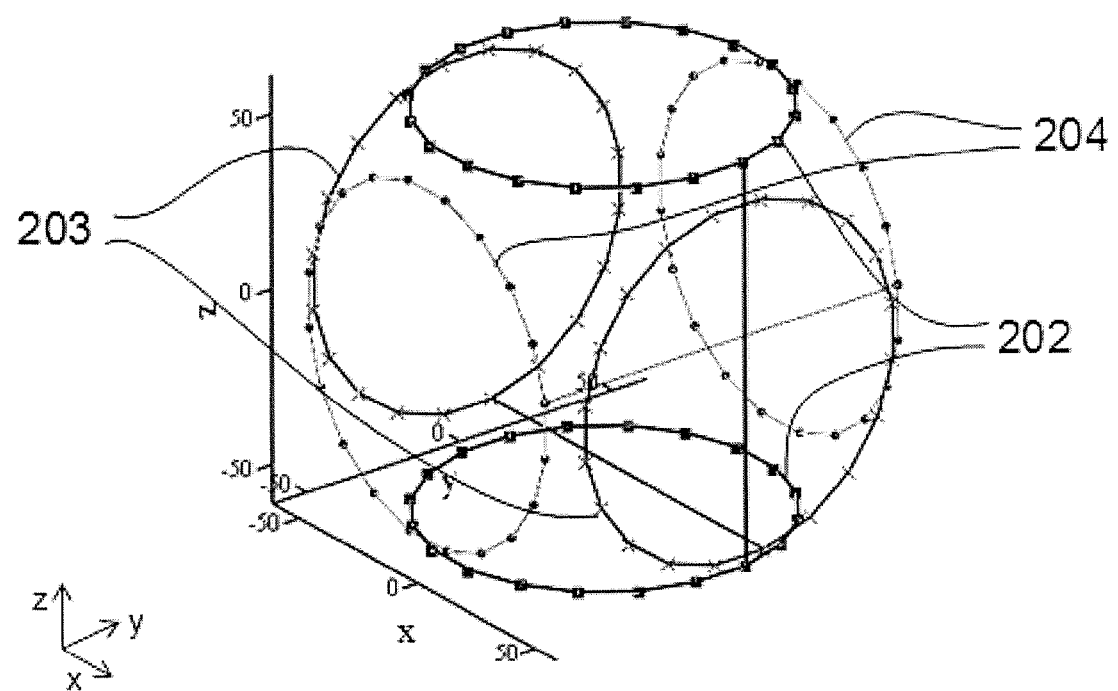
FIGS. 2a-c show an example coil arrangement for the system of the invention and associated selection fields.
Figure 2B:
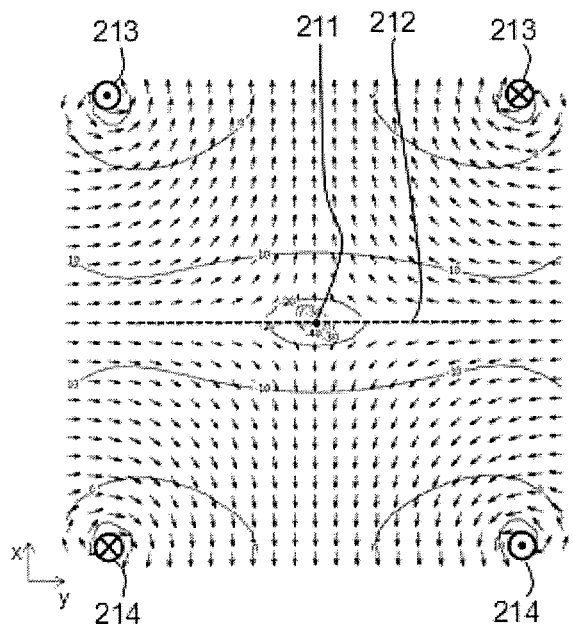
Figure 2C:
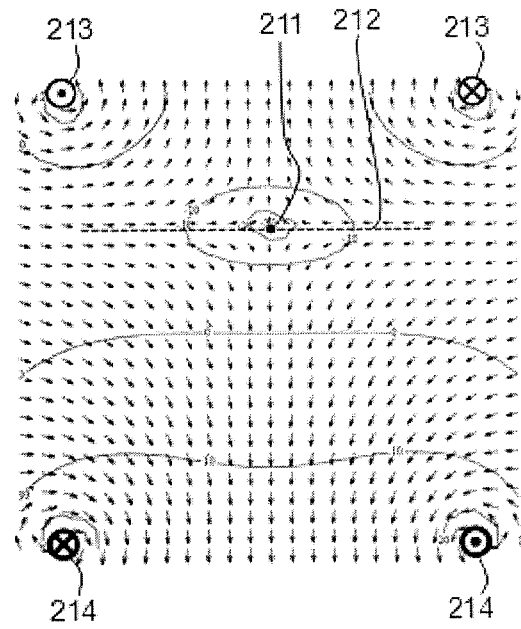

FIG. 2-c show an example coil arrangement and associated selection fields. The selection fields advantageously produce a spatially varying magnetic field with a point or line with zero field, known in magnetic particle imaging as the field-free point (FFP) or field-free line (FFL). Conceptually the simplest approach to this is a gradient field, which is most readily produced by a pair of Maxwell coils with opposing currents in the two coils. Varying the relative magnitudes of the currents moves the FFP. FIG. 2a shows a set of gradient coils with x-axis 203, y-axis 204 and z-axis 202 pairs of coils. FIGS. 2b and 2c show simulations of selection fields produced by a pair of these coils (specifically, the x-axis coils, plotted in the y-x plane, but generalizable to any pair). The arrows show the in-plane magnetic field direction and the contours are of the magnitude of field strength in 10 dB intervals. FIG. 2b shows that when the current in the first coil 213 is equal and opposite to the current in the second coil 214, the FFP 211 is located in the centre of the system. There is also a plane 212 where the x-axis component of the magnetic field ($H_x$) is zero. FIG. 2c shows the behaviour when the magnitude of the current in the second coil 214 is larger than that in the first coil 213. In this case, the FFP 211 and plane where $H_x$=0 have shifted upwards (in the positive x-direction). By superposition of fields from the three x-, y-, and z-axis coil pairs, this position and orientation of this point and plane can be adjusted. Scanning of a surface that is field-free (at least in one vector) allows a faster search for tags than would be possible using a field-free point.

Figure 3A:
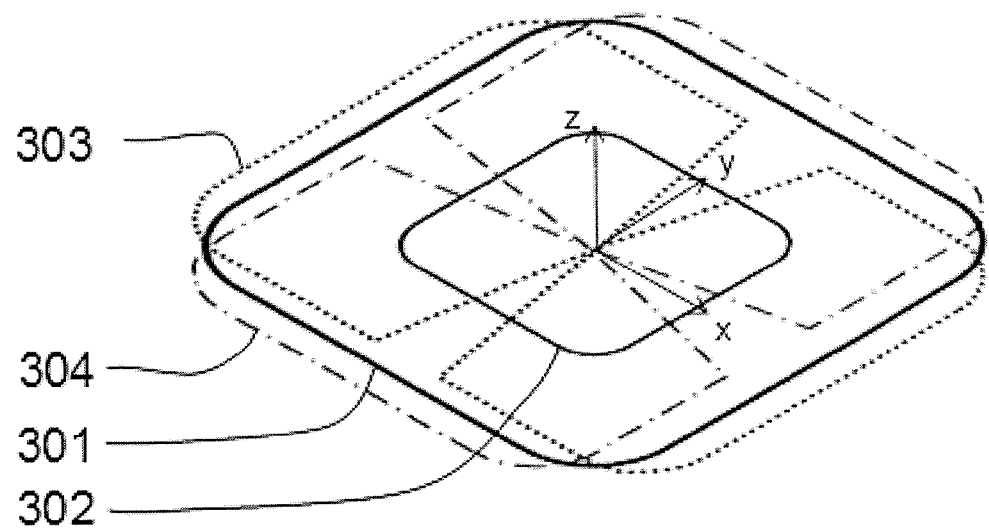
FIGS. 3a-d show example coil arrangements.
Figure 4A:
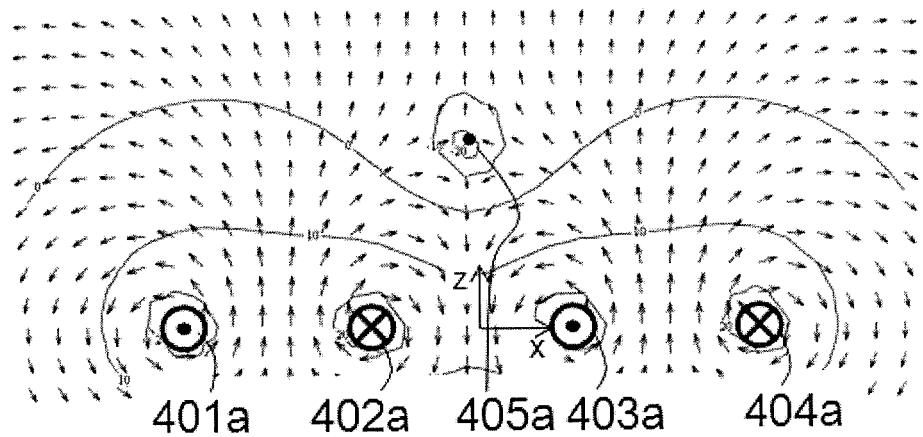
FIGS. 4a-c show the movement of a field-free point or line from a single-sided coil arrangement.
Figure 4B:
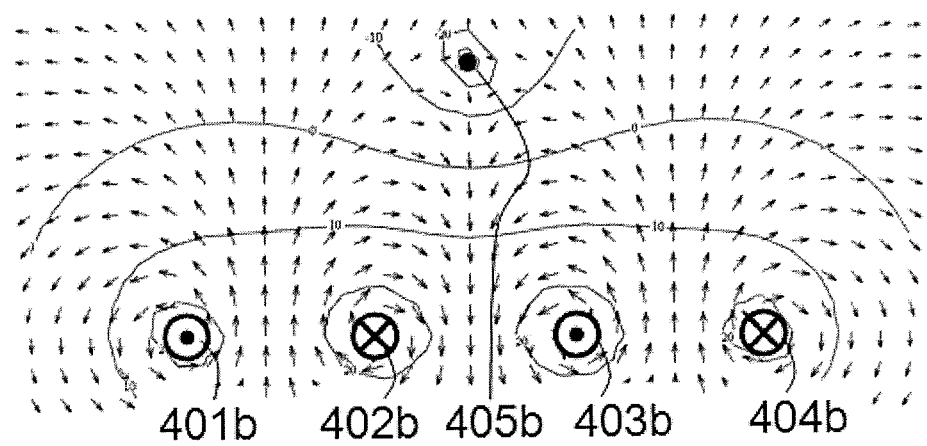
Figure 4C:
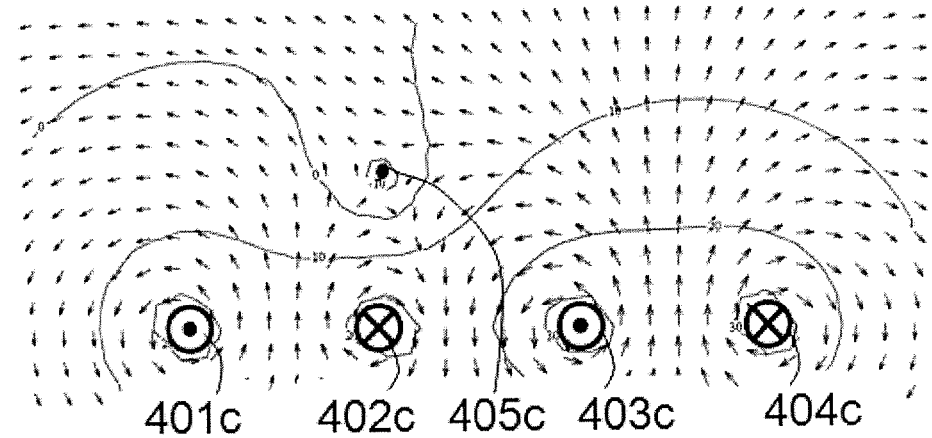

FIG. 3a shows a single-sided coil arrangement that can be employed. The selection coils are illustrated in the z=0 plane (although in practice, they have finite thickness), with the detection volume being the space above, for which z>0. The coils include a large z-axis coil 301 and a smaller z-axis adjustment coil 302, an x-axis adjustment coil 303 (dotted line), and a y-axis adjustment coil 304 (dot-dash line). The two z-axis coils 301 and 302 have opposing currents, which create a FFP on the z-axis with z>0. The fields in this case are illustrated in FIG. 4a (described in more detail later). When the magnitude of the current in the z-axis adjustment coil 302 is increased, the FFP moves in the +z direction (upwards). The fields in this case are illustrated in FIG. 4b (described later). A current in the x-axis adjustment coil 303 shifts the FFP along the x-axis. The fields in this case are illustrated in FIG. 4c (described later). Similarly, a current in the y-axis adjustment coil 304 shifts the FFP along the y-axis. Hence the FFP can be swept throughout the sensing volume to detect the location of the tag or tags.

Interrogation (AC) signals can be superimposed on these coils or may be provided by a separate coil set. Similarly, received signals may be picked up on the selection coils, on the interrogation coil(s) or on separate dedicated receive coil(s).

Figure 3B:
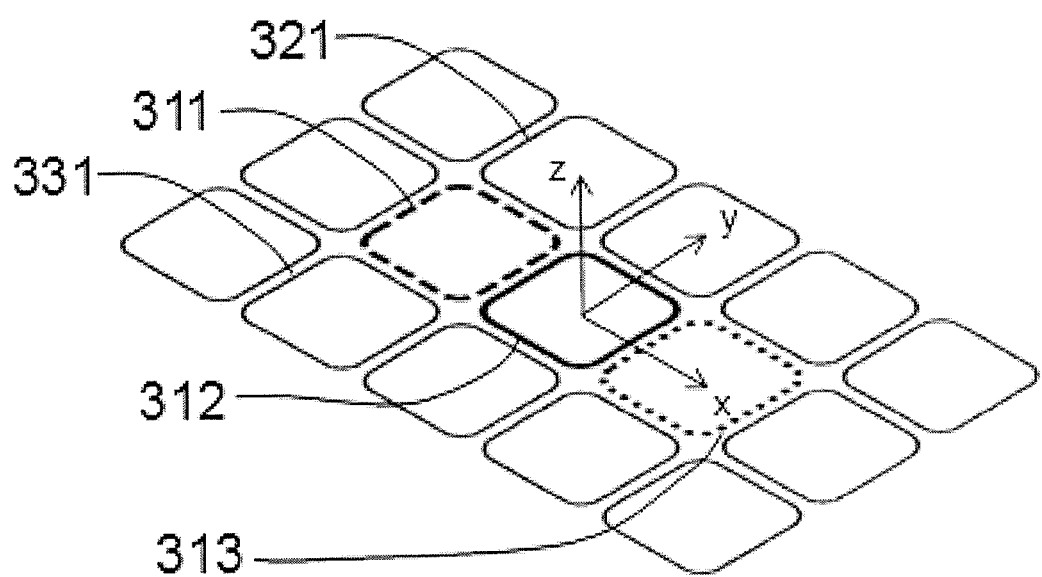

FIG. 3b shows a single-sided coil arrangement. The coils are illustrated in the z=0 plane (although in practice, they have finite thickness), with the detection volume being the space above, for which z>0. The selection coils take the form of a regular array, substantially filling the detection area. Individual control of currents to the coils in the array allow a FFP or FFL to be moved within the detection volume. A first 311 (dashed), second 312 (bold), and third 313 (dotted) coils are highlighted to illustrate the process of moving a FFP in the x-z plane. If the (anti-clockwise) relative currents in the three coils 311, 312 and 313 are 1, 0 and 1 respectively, a FFP is produced on the z-axis with z>0. The fields in this case are illustrated in FIG. 4a (described later). Adjusting the current in the second coil 312 moves the z-axis position of the FFP. Relative currents in the three coils 311, 312 and 313 of 1, −0.5, and 1 respectively move the FFP in the +z direction, as illustrated in FIG. 4b. Imbalance between the first 311 and third 313 coils moves the FFP in the x-axis. Relative currents in the three coils 311, 312 and 313 of 1, 0, and 3 respectively move the FFP in the −x direction, as illustrated in FIG. 4c. Similarly, field-free lines may be produced by driving rows of coils i.e. 311, 321, 331 with identical currents. This effectively reduces the field source a two dimensional one, and changes the FFP to a FFL. The use of a FFL can enhance scan rates for locating the tag(s).

For very high aspect ratio tags, the earth's magnetic field can be of a similar magnitude to $H_s$. Advantageously, magnetic field sensors, such as GMR sensors, are located at the centre of each coil to assist with calibration and compensation for the earth's magnetic field.

Interrogation and detection coils are advantageously separate large coils, each covering the entire detection volume (similar to 303, 304 and 301 in FIG. 3a for the x, y, and z-axes respectively).

Figure 3C:
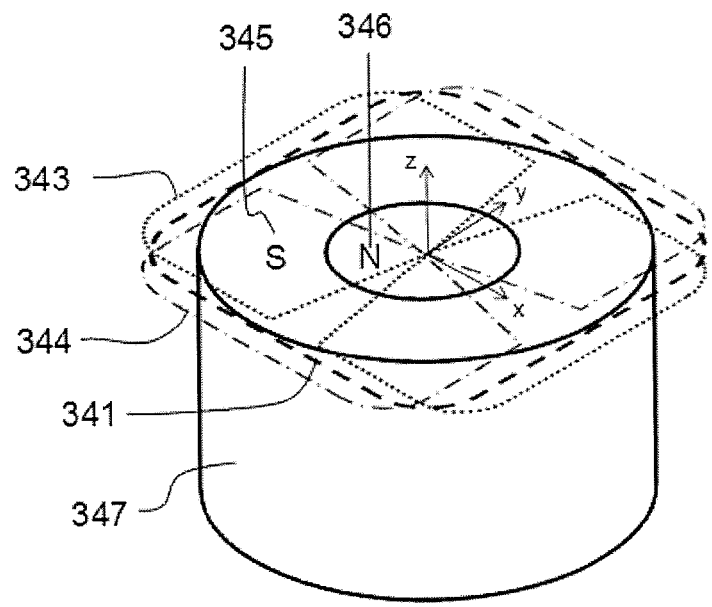

FIG. 3c shows an embodiment with permanent magnets providing the selection field, and an adjustment provided by electromagnets. A permanent magnet assembly 347 includes a central pole 346 and an annular pole 345 with opposing polarity to the central pole 346. Together these produce a FFP in on the z-axis above the x-y plane. A z-axis shift coil 341 (dashed line) moves the FFP in the z-direction. An x-axis shift coil 343 (dotted line) moves the FFP in the x-direction. A y-axis shift coil 344 (dot-dash line) moves the FFP in the y-direction.

Figure 3D:
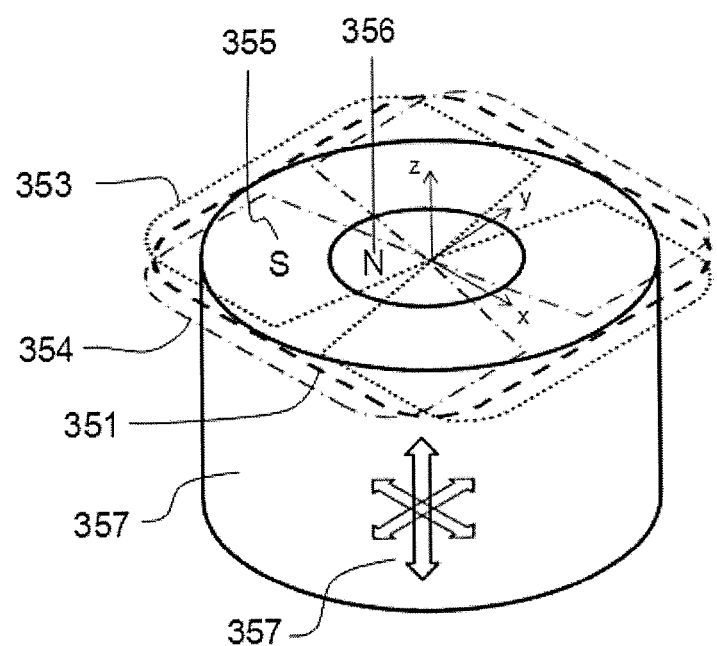

FIG. 3d shows an embodiment of the invention with permanent magnets providing the selection field. A permanent magnet assembly 357 includes a central pole 356 and an annular pole 355 with opposing polarity to the central pole 356. Interrogation coils 353, 354 and 351 provide AC interrogation fields at the FFP in the x-, y- and z-axes respectively. In order to translate the FFP, the whole assembly is mechanically moved by a motorised stage 357 or manual operator in the case of a hand-held reader.

FIGS. 4a-c show the movement of a field-free point or line from a single-sided coil arrangement according to the invention. A cross-section in the x-z plane is illustrated. The arrows show the in-plane field vector and the contours are of field strength at 10 dB intervals. First 401a,b,c, second 402a,b,c, third 403a,b,c and fourth 404a,b,c conductors pass currents into and out of the page. A FFP or FFL 405a,b,c is located in the x-z plane, moveable throughout a sensing region. In the case of short conductors, being cross-sections of loops (as in FIG. 3a), a FFP is formed. In the case of long conductors, a FFL is formed. This is similar to the case when rows of current loops are driven with the same current, e.g. in FIG. 3b, coils 311, 321 and 331 would be driven with matching currents. In FIG. 4a the relative currents through the four conductors 401a, 402a, 403a, 404a are 1,−1,1,−1 respectively. In FIG. 4b the relative currents through the four conductors 401b, 402b, 403b, 404b are 1,−1.5,1.5,−1 respectively. The FFP or FFL 405b is moved in the +z direction. In FIG. 4c the relative currents through the four conductors 401c, 402c, 403c, 404c are 1,−1,3,−3 respectively. The FFP or FFL 405c is moved in the −x direction.

Figure 5A:
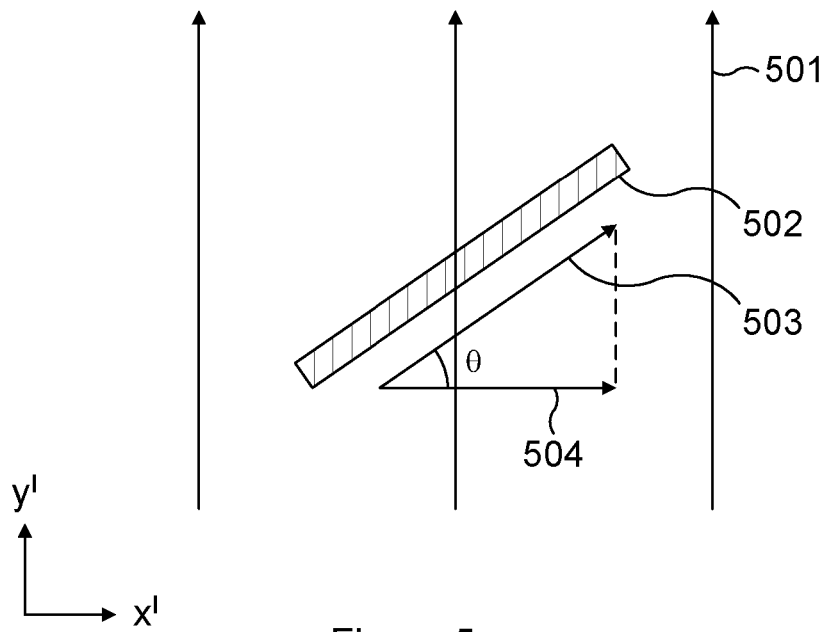
FIGS. 5a-b relate to detection of the orientation of a tag.
Figure 5B:
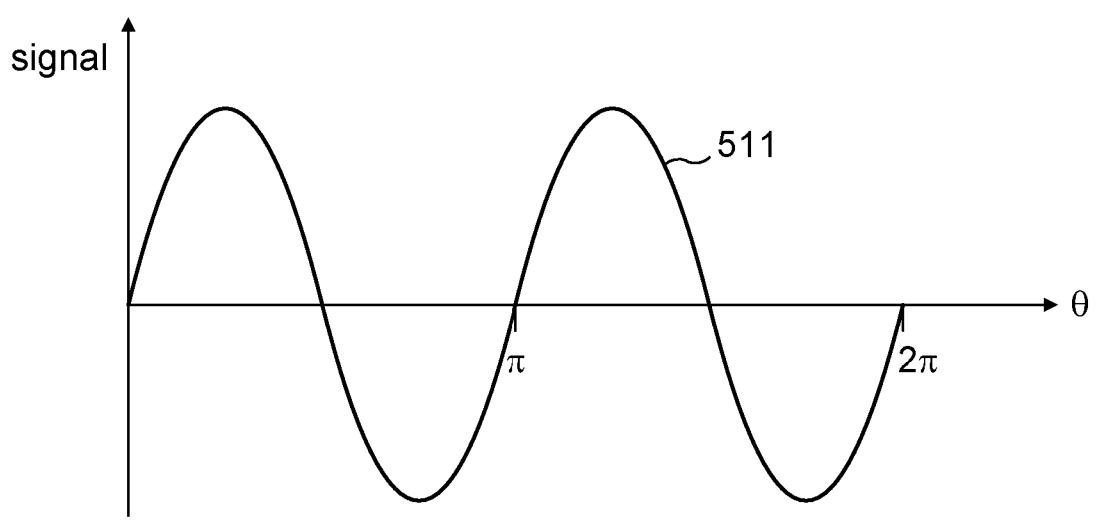

FIGS. 5a-c illustrate a method of detecting the orientation of the tag. FIG. 5a shows a tag 502, which is located at a FFP, or, as a minimal requirement, at a point where the selection field parallel to the long axis of the tag is less than $H_s$. An AC interrogation field 501 is applied in the y' direction by a transmit coil. The tag 502 becomes magnetised along its easy magnetisation axis (i.e. the long axis), inducing a dipole moment $\underline{m}$ 503. The receiver is sensitive to fields in the x' direction, orthogonal to the interrogation field. A component of the induced dipole moment 504 equal to $|\underline{m}|*\cos(\theta)$ is directed along the x' axis. The receiver is able to pick up this component of induced dipole moment 504 and related harmonics and intermodulation products with minimal interference from the interrogation field 501. Advantageously, the interrogation transmit coil also has a shim coil associated with it, which performs a fine adjustment of the balancing of transmit and receive coils. This balancing (sometimes known as dynamic nulling in other inductive sensing applications) makes it possible to tune the orthogonality of the transmit and receive coils to beyond that achieved with standard manufacturing tolerances. It also allows for dynamic removal of extraneous transmit-to-receive breakthrough due to other conductive or magnetic objects in the vicinity of the coils. FIG. 5b illustrates the magnitude of the received signal 511 as a function of the angle θ between the tag and the receive sensitivity axis. The transmit and receive fields may be rotated to detect the tag angle in different planes.

Figure 6A:
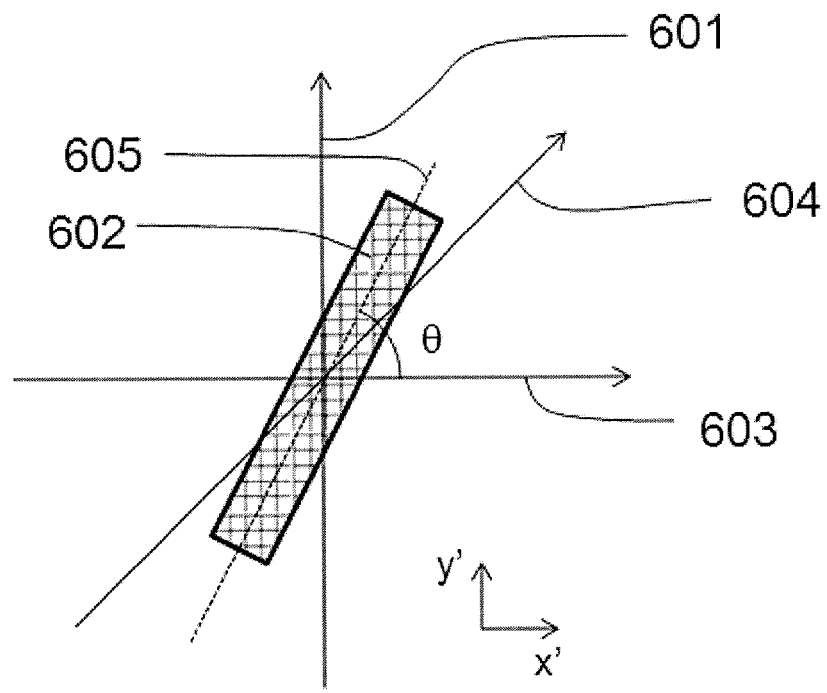
Figure 6B:
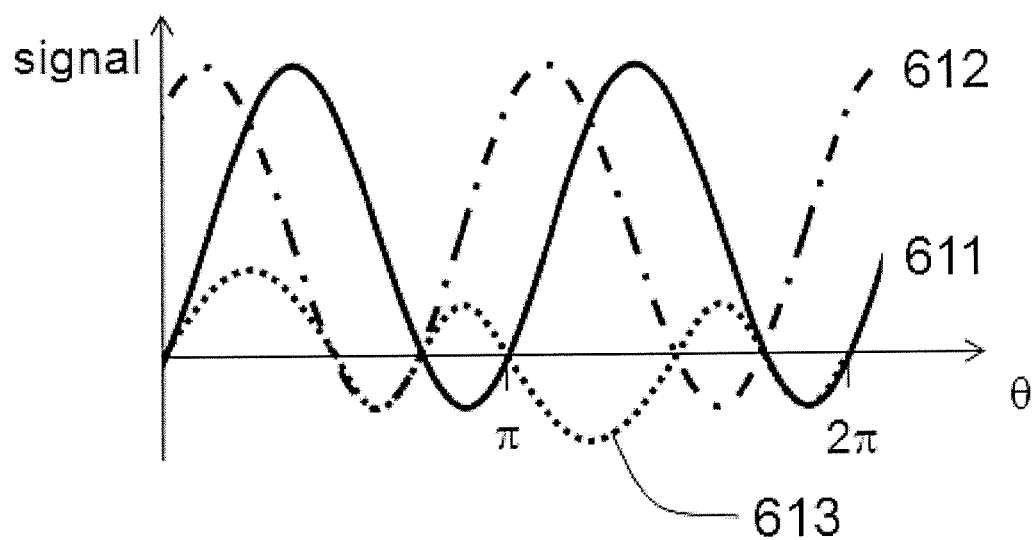

FIGS. 6a-c illustrate another method of detecting the orientation of the tag. FIG. 6a shows a tag 602, typically located at a FFP to allow detection. Transmit coils produce interrogation fields on different axes. For the purposes of describing the method, an interrogation field at frequency $f_1$ 601 is produced on the y' axis, an interrogation field at frequency $f_2$ 603 is produced on the x' axis. For full orientation information, an interrogation field at frequency $f_3$ would be transmitted on a z' axis, not in the plane of the diagram. However, this is omitted from the diagram for clarity. Receiver coils have their own axes of sensitivity at this point in space, and one with a sensitivity axis along x'=y' 604 is illustrated in this example. FIG. 6b shows the received signals by this receiver coil as a function of tag rotation angle θ. Harmonics of $f_1$ have a particular signature shown by the solid trace 611. Harmonics of $f_2$ have a particular signature shown by the dot-dash trace 612. Intermodulation products of $f_1$ and $f_2$ have a particular signature shown by the dotted trace 613. Extending to three dimensions, harmonics of $f_3$, and intermodulation products of $f_1$ & $f_3$, $f_2$ & $f_3$, and of all three frequencies have their own signatures. These signatures can be used to determine the orientation of the tag. Look-up tables of transmitter and receiver field angles at this particular point in space are used to assist with interpretation. Advantageously, pairs of frequencies are transmitted from opposite sides of the patient, so that the frequency generation sources are relatively isolated from one another and unwanted non-linear mixing within the transmitter circuits is minimised.

FIG. 6c illustrates an embodiment of the coil arrangement for the interrogation and detection coils. Selection coils are located in the region underneath the patient 621 (not shown). A large loop interrogation/detection coil is also located in this region 625. Interrogation/detection coils are located on either side of the patient. Dipole 622a&b, quadrupole 623a&b and octupole 624a&b coils are located on each side of the patient. Sets of dipole, quadrupole and octupole coils (e.g. 622a, 623a and 624a for the left side) are substantially orthogonal (balanced with respect to one another). In operation, interrogation signals at frequency $f_1$ are transmitted from a subset of the left coils 622a, 623a, 624a, interrogation signals at frequency $f_2$ from a subset of the right coils 622b, 623b, 624b, and interrogation signals at frequency $f_3$ from the z-axis interrogation coil 625. As an example measurement, coil 623a might produce an x-axis field at $f_1$, coil 624b might produce a y-axis field at $f_2$, and coil 625 would produce a z-axis field at $f_3$. The remaining coils are then used to detect intermodulation products. Coil functions would then be swapped to make other measurements.

FIGS. 7a-c illustrate another method of detecting the orientation of the tag. FIG. 7a shows a ribbon-like tag 702 oriented with the long axis approximately parallel to the z-axis, the medium axis approximately parallel to the y-axis and the short axis approximately parallel to the x-axis. FIG. 7b shows the magnitude of the harmonic (or intermodulation) response as the selection field is swept. As the selection field is swept in the z-axis, a sharp response is seen to the interrogation field 712, due to the easy magnetisation in this axis. As the selection field is swept in the y-axis, a broader response is seen 711. As the selection field is swept in the x-axis, an even smaller, broader response is seen 710 (if it is above the noise floor at all). This orientation angle dependence means that the relative responses in three sweep axes x', y', and z' can be used to estimate the orientation of the tag. This approach can be used in a uniform selection field, and so can be used to sense the orientation of a single tag without needing to locate it in space (provided all tags is present in the sensing region have the same orientation). FIG. 7c shows the harmonic response 724 as a function of ac excitation field amplitude 723 (Hex) without a selection field present. As the excitation field amplitude is increased in the z-axis, the harmonic response appears as the tag magnetisation becomes saturated 722. The harmonic response is seen at the lowest fields along the easy magnetisation axis. The harmonic response to an increasing excitation field amplitude along the y-axis is plotted 721 and emerges at a higher excitation field. The harmonic response vs. excitation field in the x-axis 720 would only be seen at the highest fields, if at all. This orientation angle dependence means that the relative responses in three sweep axes x', y', and z' can be used to estimate the orientation of the tag. For the case where the active region contains only tags with the same orientation, this can be performed without knowing the tag location. Alternatively, it can be performed in combination with a selection field to perform spatial selection.

FIGS. 8a-b illustrate tag arrangements in which the two ends of a tag can be distinguished from one another. Symmetrical tags might be oriented at 180 degrees to the intended direction, without the user being able to tell. The orientation of tapered tags can be detected due to by different responses of the thick end and the thin end, according to one of the previously described detection methods. For example, with the FFP on the thick end, response is larger than with the FFP located at the thin end of the tag. FIG. 8a shows a tapered tag, which has the advantage of being simple to manufacture, being cut from a single piece of ribbon. FIG. 8b shows an alternative tapered tag, which is more easily oriented in all three rotation axes. When the FFP is located at the junction of the T shape, an additional response is measured in along the z-axis, as well as the response along the x-axis. FIG. 8c shows a tapered tag being constructed from multiple layers, producing a different tag thickness in different regions. In this instance, the value of $H_s$ is larger at the thick end of the tag.

Figures 9A, 9B:
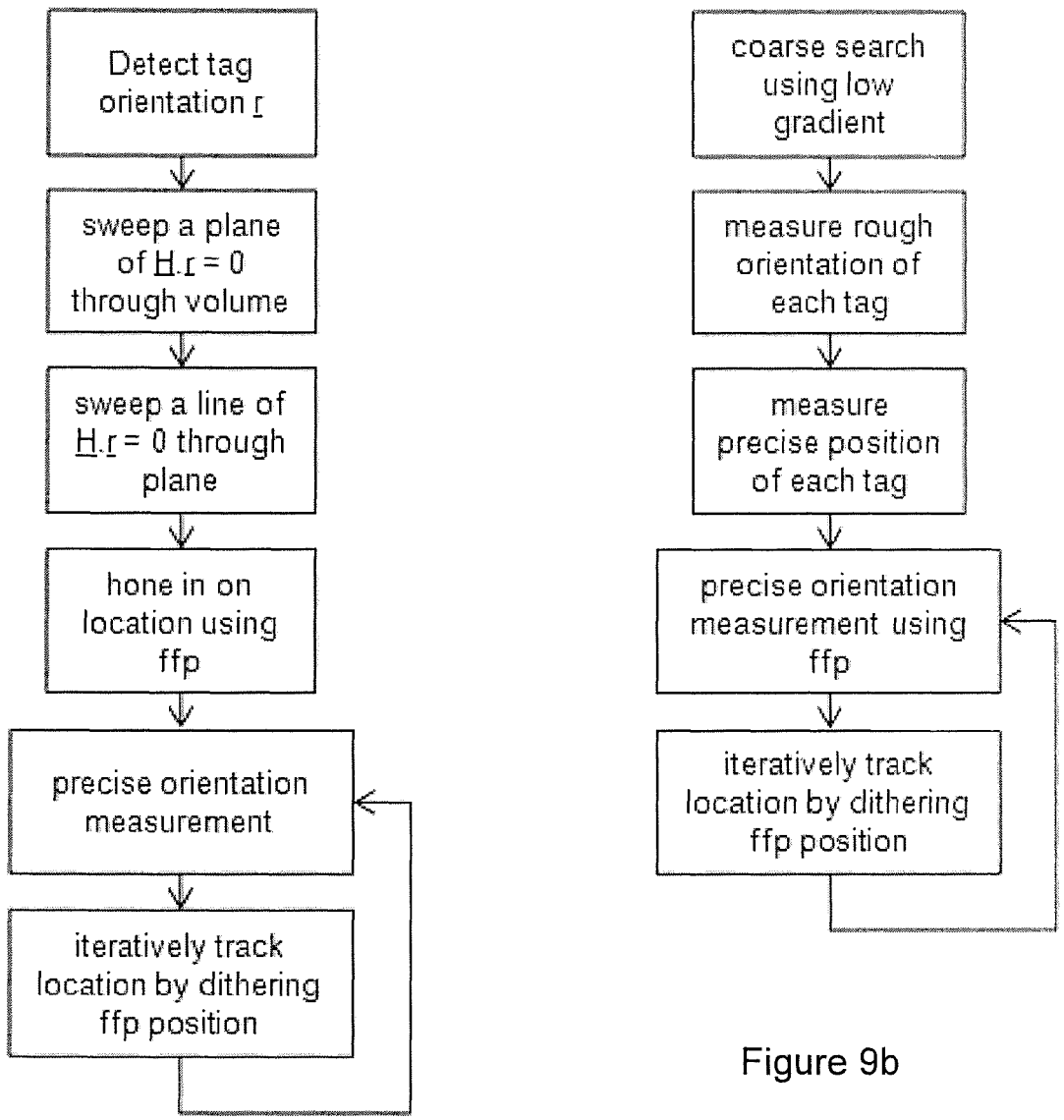
FIGS. 9a-b show flow charts of a tag tracking process according to the invention.

FIGS. 9a-b show flow charts for a tag tracking process. FIG. 9a shows a flow chart for tracking the position of a single tag within the detection volume. Firstly the tag orientation is detected (for example, as described with regard to FIGS. 7a-c), then the location is narrowed down by generating planes, lines and/or points where the field parallel to the tag orientation is zero. Finally, precise location can be tracked in real time as the tag moves by dithering location of a FFP and/or a detection angle to look for increases or decreases in tag response. FIG. 9b shows a flow chart for tracking the position of a multiple tags within the detection volume. Firstly, a coarse positional sweep is performed, using a low field gradient, giving the approximate position of each tag. Secondly, the orientation of each tag is measured. Optionally, more precise measurements of position can then be made. Finally, position and orientation of the tags are iteratively tracked in real-time, as for the case with a single tag, but with interrogation being time-division multiplexed between the different tags.

Figure 10A:
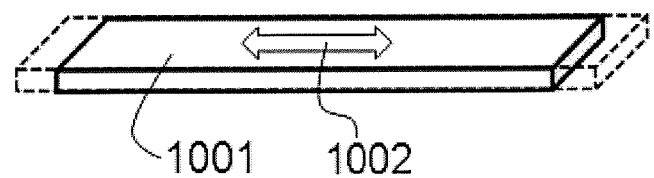
FIGS. 10a-d relate to a tag including an additional magneto-mechanical or magnetoelastic resonance.
Figure 10B:
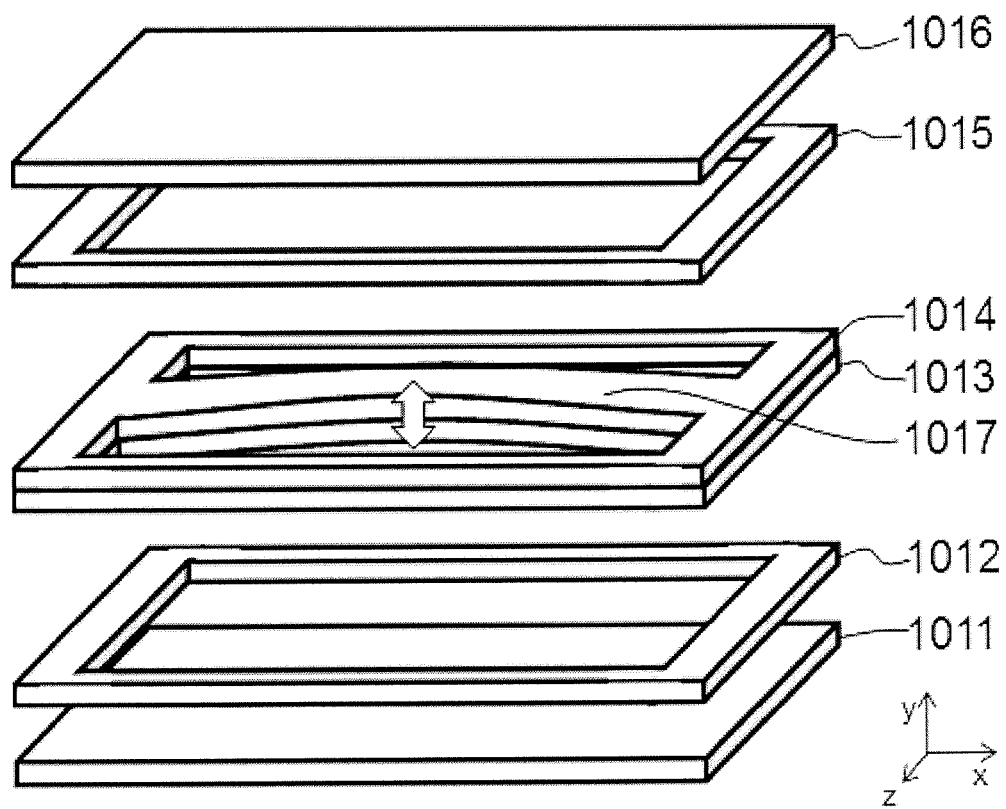

FIGS. 10a-d relate to an embodiment of the invention wherein an additional magneto-mechanical or magnetoelastic resonance is employed. FIG. 10a shows a magnetoelastic tag 1001. In operation the tag is excited into a longitudinal extensional vibration mode, as illustrated by the arrow 1002 and dotted lines. The resonant frequency of this vibration is affected by the length of the tag and the speed of longitudinal sound waves in the material, such that the tag length is half a wavelength (or a multiple thereof) at resonance. A typical speed of sound of around 4600 m/s means that a 23 mm long tag would resonate at around 100 kHz in this mode. In operation, the tag would need to be flexibly mounted, so as not to damp the mechanical vibration. This might be achieved by allowing it to vibrate freely within a box, mounting it between two foam layers, or by supporting it at a nodal location. FIG. 10b shows an exploded view of a magnetoelastic tag operating in bending mode. A magnetostrictive layer 1014 is bonded to a substrate 1013. The expansion and contraction of the magnetostrictive layer 1014 under an applied alternating field causes bending of a beam or cantilever 1017. The oscillating motion of the beam 1017 is illustrated by the double-ended arrow. In order to allow free motion of the beam within the application, the beam is mounted within a frame and within a cavity in this embodiment. The beam is provided with clearance by upper and lower spacers 1015 and 1012 respectively and sealed in by upper and lower caps 1016 and 1011 respectively. In practice the lower layers 1011, 1012 and perhaps 1013) may be formed from a micromachined or etched silicon or glass wafer and the upper layers 1015 and 1016 may be formed from a second micromachined or etched silicon or glass wafer. The bending mode embodiment has the advantage that the resonant frequency is lower, so the tag can be made smaller. For example, a 3 mm long cantilever, 0.04 mm thick has a first resonant frequency at around 10 kHz.

Figure 10C:
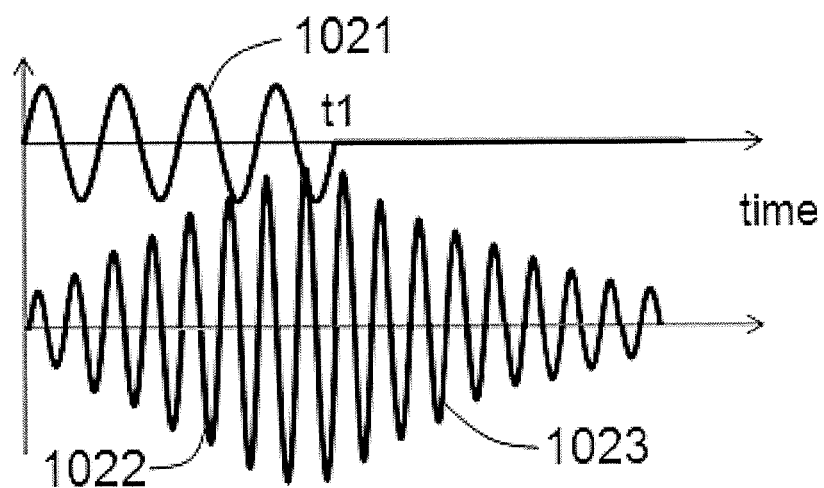

FIG. 10c shows a pulse-echo drive scheme, which allows detection of small signals from the tag during time periods when the large interrogation fields are switched off. The AC interrogation field 1021 is applied for a short time, t1. During this time, the magneto-acoustic resonant response of the tag 1022 and 1023 has a ring-up period 1022. Once the interrogation field is switched off after t1, the response of the tag continues to ring 1023, during a ring-down period, typically characterised by an exponential envelope the decay time of which is determined by the resonator quality factor. The response is shown at the second harmonic (H2), although the fundamental (H1) might be used in this embodiment. This has the advantage that the sensitive receiver circuits do not need to operate at the same time as the high power interrogation field, and do not become swamped by interfering signals.

Figure 10D:
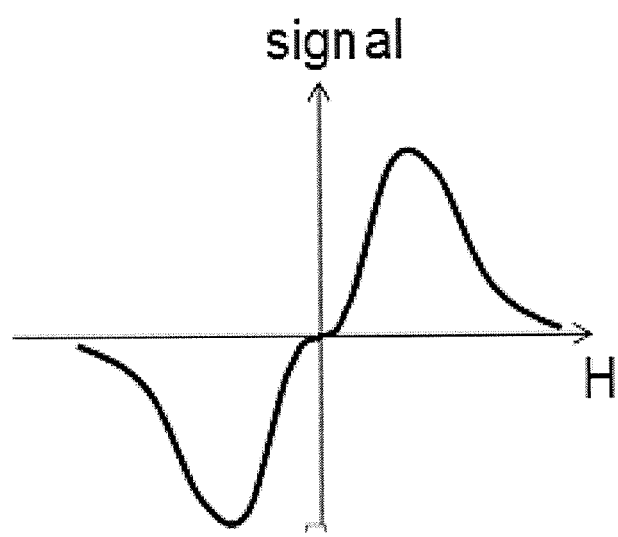

FIG. 10d illustrates the tag response (y-axis, labelled "signal") as a function of selection field (x-axis, labelled "H"), at a given AC interrogation field frequency. The frequency of the resonance is dependent on the Young's modulus of the material, which is itself dependent on the magnitude of the selection field for many magnetostrictive materials, including amorphous alloys. The degree of magnetostrictive coupling is also dependent on the magnitude of the selection field. Hence the response to a swept selection field has a characteristic signature at a given frequency, typically including a response lobe at either side of the zero field. This means that the magneto-mechanical response can be combined with the even harmonic (H2, H4, etc.) response, which also appears on either side of the selection field zero. However, it can also be used with fundamental frequency (H1), using the pulse-echo method to obtain signal.

Figure 11A:
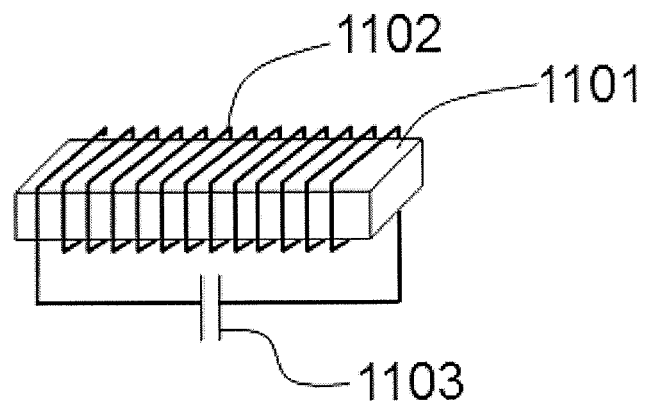
FIGS. 11a-b relate to a tag including an additional inductor-capacitor resonance.
Figure 11B:
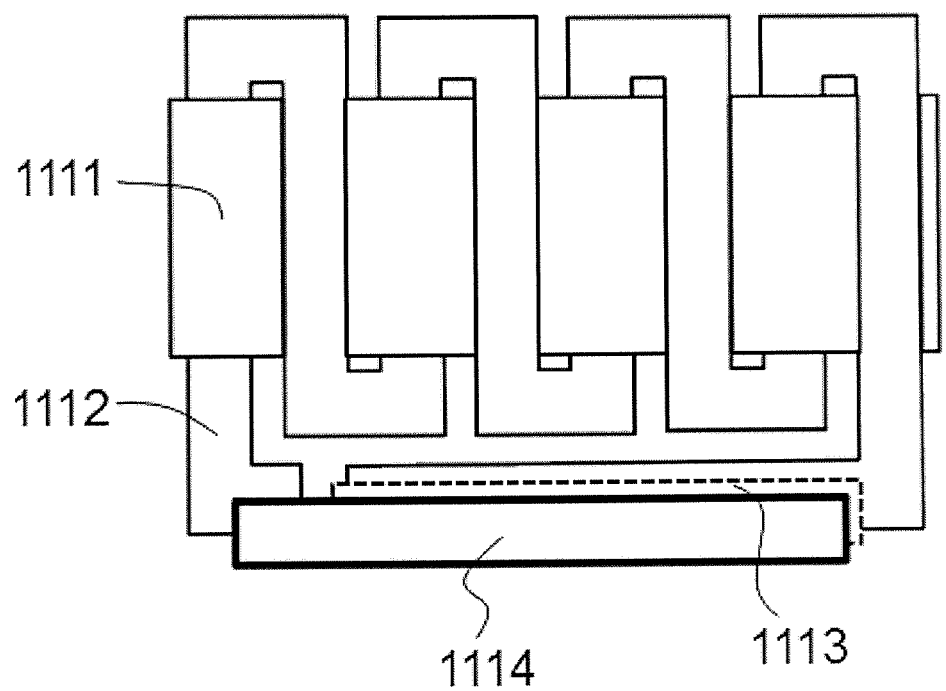

FIGS. 11a-b relate to an embodiment of the invention wherein an additional inductor-capacitor resonance is employed. FIG. 11a illustrates a tag incorporating a wound inductor 1102 and separate capacitor 1103. The inductor is formed by winding wire 1102 around a saturable permeable core 1101. When the selection field is high enough to saturate the magnetisation of the core 1101, the ac permeability drops, and hence the inductance of the inductor drops, the L-C resonant frequency $f_{LC}$ increases and the quality factor of the resonance drops. Hence the selection field can be used to select for a response from the LC resonator, by looking for an AC response at the L-C resonant frequency for an un-saturated core ($f_{LC0}$). Pulse-echo detection at the fundamental frequency (H1) or at an odd harmonic (H3, H5, etc.) of the AC interrogation field, is the preferred method of detecting this response, as illustrated in FIG. 10c.

FIG. 11b illustrates a planar tag incorporating an L-C resonator. The tag includes a saturable permeable core 1111, a printed conductor 1112 wound around core. In this embodiment, the conductor is a single foil on a substrate (not shown). The substrate is slotted and the core 1111 is woven through the substrate such that the conductor 1112 lies alternately above and below the core 1111. A planar capacitor is formed by adding a dielectric layer 1113 and a second electrode 1114 to form a parallel plate capacitor over part of the tag. This tag would operate in the same manner as the variant shown in FIG. 11*a*.

Figure 12A:
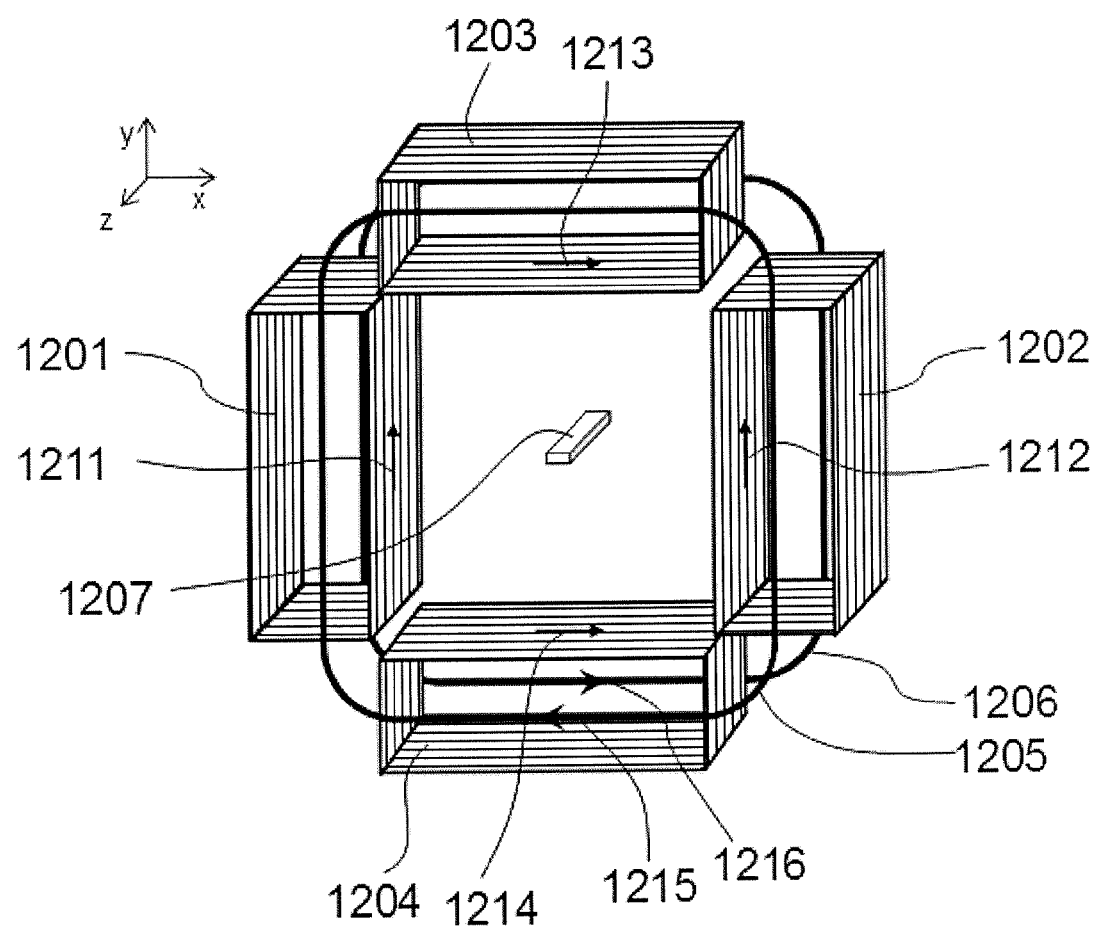
FIGS. 12a-b show a further coil arrangement according to the invention and associated selection fields.
Figure 12B:
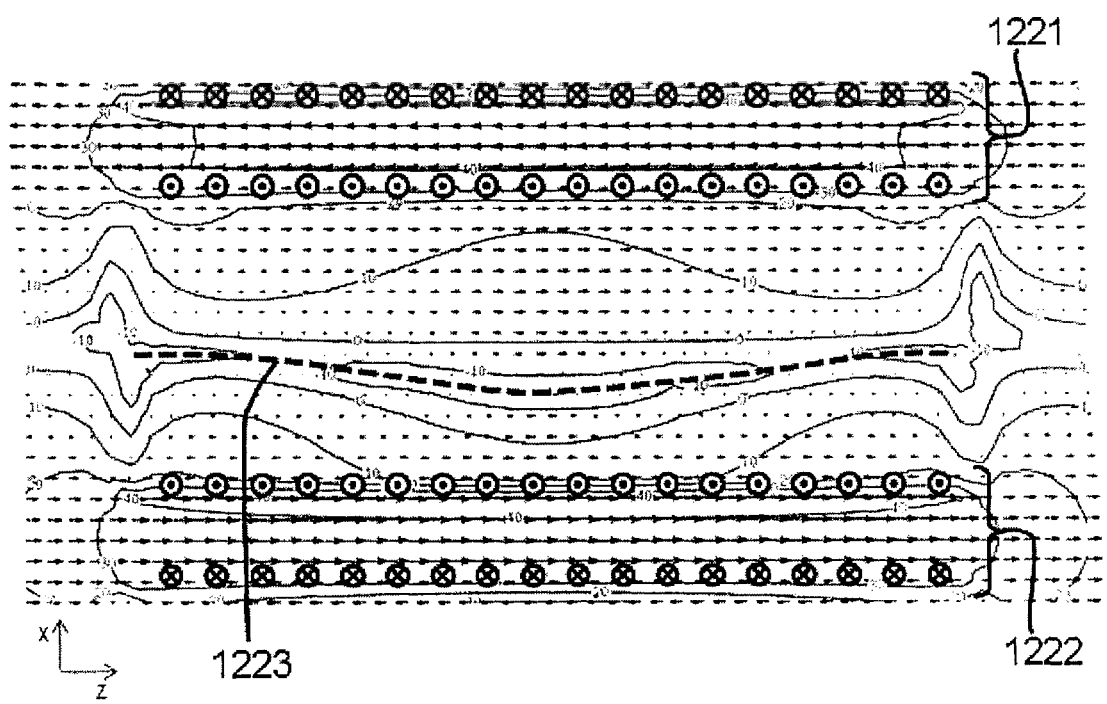

FIGS. 12*a*-*b* illustrate an example coil arrangement and associated selection fields. This embodiment is of particular benefit when the orientation of the tag 1207 is constrained so that the long axis lies along the z-axis, as shown. Only the selection field coils are shown: interrogation fields generation and tag detection could either be performed using the same coils or using additional coils and/or field sensors. The system includes a first x-axis selection coil 1201, in the form of a rectangular solenoid coil. The solenoid axis is along the z-axis and the current on the inner surface 1211 is in the +y direction. A second x-axis selection coil 1202 lies on the opposite side of the sensing region with its current 1212 in the same direction. A first y-axis sensing coil 1203 is also a rectangular solenoid with its axis along the z-axis. The current on the inner face of the first y-axis selection coil 1203 is in the +x direction, as shown by the arrow 1213. The second y-axis selection coil 1204 lies on the opposite side of the sensing volume and has it's current on the inner face 1214 in the same direction as the first y-axis selection coil. The z-axis selection coils 1205 and 1206, are conventional gradient coils (for example anti-Helmholtz coils) with currents 1215 and 1216 in opposite directions.

FIG. 12*b* illustrates the functioning of one pair of the solenoidal selection coils. A cross-section of the x-z plane is shown, with arrows indicating the component of the magnetic field along the z-axis ($H_z$). The contours show logarithmic contours of the magnitude of $H_z$. The first x-axis selection coil 1221 has as currents flowing into and out of the page as shown by the cross and dot symbols respectively. The second x-axis selection coil 1222 lies on the opposite side of the sensing volume. A slice, lying approximately in the y-z plane for which $H_z=0$ is shown as a dashed line 1223. The location of this $H_z=0$ slice 1223 is determined by the ratio of the current in the first x-axis selection coil 1221 to the current in the second x-axis selection coil 1222. In the example shown, the $H_z=0$ slice 1223 has been moved below the mid-line by applying 20% greater current in the first x-axis selection coil 1221 relative to the second x-axis selection coil 1222.

For tags oriented along the z-axis, signals are received at (or close to) the $H_z=0$ point in a selection field sweep. Moving the $H_z=0$ slice allows rapid selection and location of tags in space. The $H_z=0$ slice can be moved along the x-axis using these x-axis selection coils 1201&1202, or equivalently, 1221&1222, allowing the x-co-ordinate of tags to be found. Similarly, sweeping of $H_z=0$ slices along the other axes using the other pairs of selection coils can be used to rapidly locate tags in three dimensional space.

Figure 13:
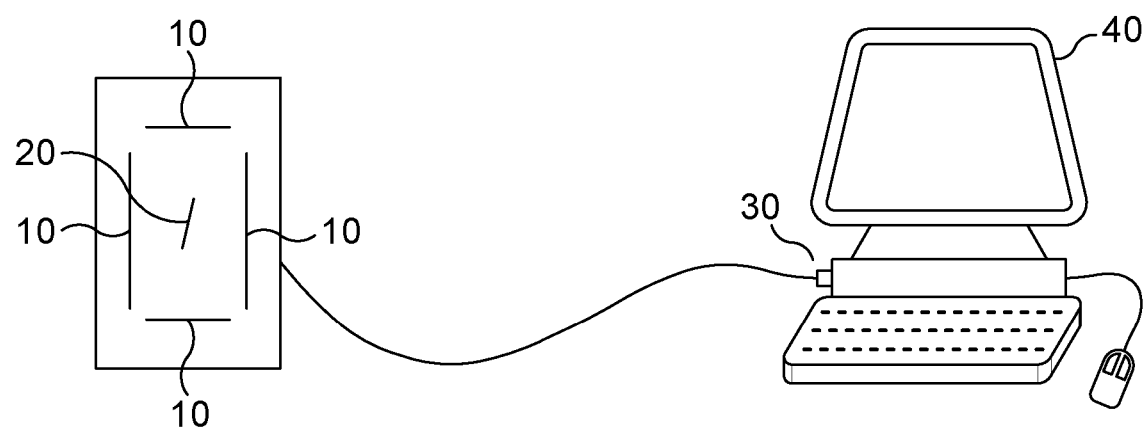
FIG. 13 is a schematic diagram showing the system of the invention and its main components.

FIG. 13 shows the system of the present invention, with coils 10, tag 20 and processing and control means 30. The processing and control means 30 communicates with coils 10 to provide the necessary driving signals in accordance with the approaches described above and receives outputs from the relevant coils 10. The outputs are processed and means 30 provides an output to a display 40 indicating the location and orientation of the tag.

An example approach taken to process the output of the coils will now be explained. For each configuration of the magnetic fields in the coils 10, some period of time of data is captured throughby the processing means 30. The longer the period of time that is captured, the better the signal to noise ratio. The range of 10-100 ms of data has been found to produce good results The frequency of the fundamental frequency of the relevant magnetic field is assumed to be known a priori. From this the fundamental and several harmonic signals are synthesised for the same number of samples as were captured by the processing means 30. These are the reference signals. The reference signals are single sided—supported on the negative half of the frequency axis (i.e. of the form exp(−j*ω*t)). Being single sided means the phase is estimated as well as the amplitude so it is not necessary to know the phase of the reference signals, only the frequency (the amplitude of the orthogonal sine and cosine components are estimated independently—giving the phase).

The inner product is taken of the captured data and each of the reference signals, giving the phase and amplitude of the the fundamental and the harmonics. This can be considered in several ways, it is the "Fourier transform" at each spot frequency (the harmonics and the fundamentals); Equivalently it is signal, downmixed to baseband, and then averaged over time (which is why longer acquisitions reduce the noise); Alternatively, since all the reference signals are approximately orthogonal, this is also equivalent to the least squares fit to the reference signal. Using these approaches the processing system can readily determine tag position and location.

As will be appreciated from the above, the present invention provides a system which can locate and determine the orientation of a tag in a simple and effective manner. It can operate with a tag which can be small and of a structure which enables it to be employed with medical devices that can be inserted easily into a body.

The invention claimed is:

1. A method for determining a magnetic tag location and a magnetic tag orientation of at least one magnetic tag of a plurality of magnetic tags the method comprising steps of:
   providing the plurality of magnetic tags, each of the plurality of magnetic tags having an elongated shape with an aspect ratio between a first edge and a second edge of at least 1000:1;
   providing a system having a single-sided coil arrangement with a plurality of planar coils that, when DC current is applied thereto, create a selection field and, when AC current is applied thereto, create an interrogation field, the system including
      at least one first planar coil for controlling a field-free point (FFP) or a field-free line (FFL) and for generating a first interrogation field at a first frequency,
      at least one second planar coil for controlling the FFP or the FFL and for generating a second interrogation field at a second frequency, wherein the at least one first planar coil and the at least one second planar coil are co-planar,
      at least one third planar coil for generating a third interrogation field at a third frequency, wherein the single-sided coil arrangement is configured to generate the selection field and the interrogation field,
      at least one processor for receiving and processing detection signals from a plurality of receiver coils to determine the magnetic tag location and the magnetic tag orientation of the at least one magnetic tag, and
      a display in communication with the at least one processor, and for displaying an indication of the magnetic tag location and the magnetic tag orientation of the at least one magnetic tag;
   applying, by the at least one processor of the system, the DC current with a varying magnitude to one or more of the plurality of planar coils arranged on a plane to create the selection field within a detection volume, wherein the selection field varies to move the FFP or the FFL to a position approximating the magnetic tag location for the at least one magnetic tag;

applying, by the at least one processor of the system, the AC current to the one or more of the plurality of planar coils to generate the interrogation field within the detection volume, wherein the first interrogation field is produced at the first frequency, the second interrogation field is produced at the second frequency, and the third interrogation field is produced at the third frequency, and wherein each of the first frequency, the second frequency, and the third frequency is distinct;

determining, by the at least one processor of the system, harmonic responses as a function of excitation field amplitude, for the at least one magnetic tag in three sweep axes by:
  detecting first harmonics of the first interrogation field at one or more of the plurality of receiver coils,
  detecting second harmonics of the second interrogation field at the one or more of the plurality of receiver coils, and
  detecting third harmonics of the third interrogation field at the one or more of the plurality of receiver coils;

determining, by the at least one processor of the system, the magnetic tag location for the at least one magnetic tag based on the first harmonics, the second harmonics, and the third harmonics by:
  generating, by each of the first interrogation field, the second interrogation field, and the third interrogation field, a first magnetic response at the at least one magnetic tag of the plurality of magnetic tags, wherein the first magnetic response comprises a first width and is associated with a first axis of the at least one magnetic tag;
  generating, by each of the first interrogation field, the second interrogation field, and the third interrogation field, a second magnetic response at the at least one magnetic tag of the plurality of magnetic tags, wherein the second magnetic response comprises a second width and is associated with a second axis of the at least one magnetic tag, and
  generating, by each of the first interrogation field, the second interrogation field, and the third interrogation field, a third magnetic response at the at least one magnetic tag of the plurality of magnetic tags, wherein the third magnetic response comprises a third width and is associated with a third axis of the at least one magnetic tag;
  comparing, for the at least one magnetic tag, the first width, the second width, and the third width to determine a shortest width when the FFP or the FFL is at the magnetic tag location;
  identifying, for the at least one magnetic tag, which of the first axis, the second axis, or the third axis is associated with the shortest width;
  determining, for the at least one magnetic tag, a long axis of the at least one magnetic tag based on the identifying of which of the first axis, the second axis, or the third axis is associated with the shortest width;
  identifying, for the at least one magnetic tag, which of the first axis, the second axis, and the third axis corresponds to the long axis;
  determining, for the at least one magnetic tag, the magnetic tag orientation of the least one magnetic tag based on the identifying of which of the first axis, the second axis, and the third axis corresponds to the long axis; and transmitting, by the at least one processor of the system, the indication of the magnetic tag location and the magnetic tag orientation of the at least one magnetic tag to the display.

2. The method according to claim 1, wherein the first harmonics and the second harmonics comprise even harmonics.

3. The method according to claim 1, wherein the FFP or the FFL is located between a pair of the plurality of planar coils comprising the at least one first planar coil and the at least one second planar coil, and wherein the FFP or the FFL is moved to the magnetic tag location and aligned with the magnetic tag orientation by varying the DC current in the at least one first planar coil relative to the DC current in the at least one second planar coil.

4. The method according to claim 1, further comprising tracking the plurality of magnetic tags within the detection volume concurrently in real time by applying the interrogation field to the detection volume for each FFP or FFL location associated with each of the plurality of magnetic tags in a time-division multiplexed manner.

5. The method according to claim 1, wherein the elongated shape is tapered.

6. The method of claim 1, wherein the single-sided coil arrangement further comprising the at least one third planar coil is further configured for controlling the FFP or the FFL and for generating the third interrogation field at the third frequency in a z-axis direction, and wherein the at least one third planar coil is co-planar with the at least one first planar coil and the at least one second planar coil.

7. The method of claim 6, further comprising an adjustment planar coil, wherein the adjustment planar coil is smaller than the at least one third planar coil and wherein the at least one third planar coil and the adjustment planar coil conduct currents in opposite directions.

8. The method of claim 6, wherein the at least one first planar coil, the at least one second planar coil, and the at least one third planar coil are configured to transmit the selection field and the interrogation field and to receive the detection signals.

9. The method of claim 1, wherein the at least one first planar coil and the at least one second planar coil are located on an x-y plane located at $z=0$, wherein the detection volume is generated above the at least one first planar coil and the at least one second planar coil where $z>0$.

10. The method of claim 1, wherein the plurality of receiver coils is oriented to detect magnetic fields orthogonal to a transmission direction of the at least one first planar coil or the at least one second planar coil.

11. The method of claim 1, the single-sided coil arrangement further comprising a plurality of first planar coils and a plurality of second planar coils arranged in a regular array.

12. The method of claim 11, wherein an FFP location or an FFL location in a z-axis direction is controlled by a magnitude of DC currents conducted through the plurality of first planar coils and the plurality of second planar coils.

13. The method of claim 1, wherein the elongated shape is tapered such that a first short edge is shorter than a second short edge.

14. The method of claim 1, wherein the elongated shape is tapered such that a first short edge is thicker than a second short edge.

15. The method of claim 1, wherein the elongated shape is T-shaped such that a first short edge is shorter than a second short edge.

16. The method of claim 1, wherein the three sweep axes correspond to an x-axis, a y-axis, and a z-axis of the at least one magnetic tag.

17. The method of claim 1, wherein the first magnetic response, the second magnetic response, and the third magnetic response are harmonic responses.

* * * * *